United States Patent [19]
Broekhof et al.
[11] Patent Number: 4,650,604
[45] Date of Patent: Mar. 17, 1987

[54] PERFUME COMPOSITION AND PERFUMED PRODUCTS WHICH CONTAIN ONE OR MORE O-ALKOXYPHENOLS AS PERFUME COMPONENT

[75] Inventors: Nicolaas L. J. M. Broekhof, Naarden; Antonius J. A. van der Weerdt, Huizen, both of Netherlands

[73] Assignee: 501 Naarden International N.V., Naarden-Bussum, Netherlands

[21] Appl. No.: 787,978

[22] Filed: Oct. 16, 1985

[30] Foreign Application Priority Data

Oct. 23, 1984 [NL] Netherlands ......................... 8403220

[51] Int. Cl.[4] ......................... A61K 7/46; C07C 43/23

[52] U.S. Cl. ................................ 252/522 R; 568/650; 568/658

[58] Field of Search .................... 252/522 R; 568/652, 568/650

[56] References Cited

U.S. PATENT DOCUMENTS 3,947,603 3/1976 Winter et al. ....................... 568/652
4,154,769 5/1979 Bauer et al. ......................... 568/652

FOREIGN PATENT DOCUMENTS 1018319 1/1966 United Kingdom ................ 568/652

OTHER PUBLICATIONS

Arctander, S., "Perfume and Flavor Chemicals", (Aroma Chemicals), 1969, nr. 705, 944, 1136, 1251, 2704.

Rigaud, J., et al, "Volatiles of Chervil Aroma", Chemical Abstracts, vol. 97, No. 18, Nov. 1982, 97:150553z.

Proksch, P., et al, "Further Oxygenated Compounds in the Essential Oil of Cistus Ladanifer L. (Cistaceae)", Chemical Abstracts, vol. 93, No. 24, Dec. 1980, 93:225491f.

*Primary Examiner*—Werren B. Lone
*Attorney, Agent, or Firm*—Brumbaugh, Graves, Donohue & Raymond

[57] ABSTRACT

Perfume compositions and perfumed products characterized by a content of one or more fragrances which have the characteristic odor of vanilla and correspond to the formula

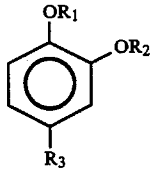

wherein $R_1$ and $R_2$ represents a hydrogen atom and the other symbol an ethyl or propyl group and $R_3$ represents a methyl or ethyl group.

12 Claims, No Drawings

PERFUME COMPOSITION AND PERFUMED PRODUCTS WHICH CONTAIN ONE OR MORE O-ALKOXYPHENOLS AS PERFUME COMPONENT

The invention relates to perfume compositions which contain one or more o-alkoxyphenols as perfume component and to products perfumed with one or more of these compounds or with the said compositions.

The solar character of vanilla is highly valued in perfumery and is therefore important from an economic point of view. To impart this order character to a perfume composition or to a product to be perfumed, use ethylvanillin or a combination of the two are normally used. These compounds are, however, not stable in alkaline media such as soap. Thus, if perfumes containing vanillin or ethylvanillin are used in toilet soap, after a short time an odor deviation and a strong brown discoloration therefore occur and after some time the vanilla character has completely disappeared.

There is therefore a demand for fragrance materials which both have the odor of vanilla and are chemically stable.

Surprisingly, it has now been found that alkylsubstituted o-alkoxyphenols with the formula

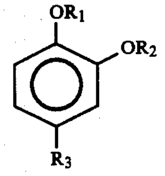

wherein one of $R_1$ or $R_2$ represents a hydrogen atom and the other symbol an ethyl or propyl group and $R_3$ represents a methyl or ethyl group, are valuable fragrance materials with the characteristic odor of vanilla.

Various alkyl-substituted alkoxyphenols are known as fragrance and/or flavoring materials. Thus, in "Perfume and Flavor Chemicals" S. Arctander names 4-methylguaiacol (No. 705), 4-propylguaiacol (No. 944), ortho-ethoxyphenol (No. 1136), 4-ethylguaiacol (No. 1251) and 5-propyl-2-ethoxyphenol (No. 2704).

In general, these compounds are characterised by spicy (clove/eugenol), phenolic and leathery or smokey odor notes, in some cases also by a vanilla-like note. A number of these compounds are therefore used in flavor compositions to supplement the taste of vanillin in synthetic vanilla flavors. None of them, however, can impart to a perfume composition a complete odor of vanilla free of all types of annoying additionally notes. They are therefore unsuitable as substitutes for vanillin.

The Dutch Patent Application No. 72.09426 states that 2-propoxyphenol is suitable for imparting a smoke flavor to foodstuffs. The Dutch Patent Application No. 72.13842 states that substituted phenols are used in the perfume and flavor industry and that there is therefore a need for vinylguaiacol without specifying in more detail for what purpose this compound and other compounds named in the application are used.

Finally, in the Dutch Patent Application No. 75.04532 a number of 2-alkoxy-4-butenyl- and methylpropenylphenols are described with floral (carnation-like) odors with leathery, oak-moss and smoky and in some cases also vanilla-like notes.

This state of the prior art, however, gives no cause for any supposition that precisely the compounds according to the present invention would be particularly suitable for imparting the odor characteristics of natural vanilla to perfume compositions.

The compounds according to the invention may be prepared according to methods described in the literature for these and similar compounds. For example, the synthesis of 2-ethoxy-4-methylphenol by catalytic reduction of ethylvanillin is described by C. H. Shunk et al. in J. Am. Chem. Soc. 82 (1960), page 5917.

A similar method of synthesis is described by G. R. Clemo et al. in J. Chem. Soc. 1952, page 3844 et seq.. Starting from isoethylvanillin (S. Arctander No. 1364), 2-ethoxy-5-methylphenol can be obtained in the same way.

The compounds mentioned above, and the corresponding 2-propoxy compounds, can also be prepared by alkylation of 4-methylcatechol with an ethyl or propyl halide or another conventional alkylating agent. In this way a mixture of 2-ethoxy-4-methyl- and 2-ethoxy-5-methylphenol or 2-propoxy-4-methyl- and 2-propoxy-5-methylphenol is obtained.

Starting from 3,4-dihydroxybenzaldehyde, 3,4-dihydroxystyrene can be prepared with a Wittig reaction. This can subsequently be converted into 4-ethylcatechol by catalytic reduction. This compound can be alkylated as mentioned above to form a mixture of 2-ethoxy-4-ethyl- and 2-ethoxy-5-ethylphenol or 2-propoxy-4-ethyl- and 2-propoxy-5-ethylphenol. In addition 2-ethoxy-4-ethyl- and 2-ethoxy-5-ethylphenol can be prepared by subjecting ethylvanillin or isoethylvanillin to a Wittig reaction and to a catalyst reduction as described above for 3,4-dihydroxybenzaldehyde.

Variations in the above-named synthesis routes, as well as various other routes not named, are obvious to the expert in the field of organic chemistry methods of synthesis. The mixtures of isomers obtained by some of the above-named methods of synthesis can be separated in a conventional manner, for example by means of chromatographic techniques, into the two components.

The compounds according to the invention are powerful fragrance material with the characteristic ordor of vanilla. They are also distinguished by their high chemical stability, especially in alkaline media such as soap, and are therefore very suitable for use in perfumes and products in which the conventional vanilla fragrances are not usable or only usable to a very limited extent. Especially the compounds in which both $R_3$ and $R_1$ and $R_2$ represent an ethyl group are characterised by their pleasant odor of vanilla which even exceeds the odor of vanillin in naturalness.

Although the odor of the two isomers in the mixtures obtained by some synthesis methods are not entirely identical, separation of the isomers is in many cases not necessary or even undesirable because precisely the mixtures are often very suitable for imparting a complete vanilla note to a perfume composition.

In this connection the term "perfume composition" means a mixture of fragrance materials and optionally auxiliary substances, if desired dissolved in a suitable solvent or mixed with a powdery substrate, which is used to impart the desired odor to the skin and/or all types of products. Examples of such products are: soaps, detergents, air fresheners, room sprays, pomanders, candles, cosmetics such as creams, ointments, toilet waters, pre- and after-shave lotions, talcum powders, hair care agents, body deodorants and antiperspirants.

Fragrance materials and mixtures of fragrance materials which can be used in combination with the compounds according to the invention for the production of perfume compositions are for example: natural products such as essential oils, absolutes, resinoids, resins, concretes etc., but also synthetic fragrance materials such as hydrocarbons, alcohols, aldehydes, ketones, ethers, acids, esters, acetals, ketals, nitriles etc., including saturated and unsaturated compounds, aliphatic, carbocyclic and heterocyclic compounds. Examples of fragrances which can be used in combination with the compounds according to the invention are: geraniol, geranyl acetate, linalool, linalyl acetate, tetrahydrolinalool, citronellol, citronnellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butyl-phenyl)propanal, 2-methyl-3-(p-isopropylphenyl)propanal, 3-(p-tert-butylphenyl)-propanal, tricylcodecenyl acetate, tricyclodecenyl propionate, 4-(4-hydroxy-4-methylpentyl)-3-cyclohexancarbaldehyde, 4-(4-methyl-3-pentenyl)-3-cyclohexenecarbaldehyde, 4-acetoxy-3-acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenylacetaldehyde, dimethylacetal, phenylacetadehyde diethylacetal, geranylnitrile, citronellylnitrile, cedryl acetate, 3-isocamphylcyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylionones, irones, cis-3-hexenol and esters thereof, indan musks tetralin musks, isochroman musks, macrocyclic ketones, macrolactone musks, ethylene brassylate, and aromatic nitromusks.

Auxiliary substances and solvents which can be used in perfume compositions which contain compounds according to the invention are, for example: ethanol, isopropanol, diethyleneglycol monoethyl ether, diethyl phthalate, etc.

The quantities in which the compounds according to the invention can be used in perfume compositions or products to be perfume can vary within wide limits and depend inter alia on the nature of the product in which the fragrance material is used, on the nature and quantity of the other components in the perfume composition and on the odor effect aimed at. It is therefore only possible to specify very rough limits which, however, provide the expert with sufficient information to be able to use the compounds according to the invention independently. In most cases a quantity of only 10 ppm in a perfume composition will already be sufficient to achieve a clearly perceptable odor effect. On the other hand, to achieve special odor effects, it is possible to use quantities of 25% by weight or even more in a composition. In products perfumed with perfume compositions these concentrations are porportionally lower, depending on the quantity of composition used in the product.

The following examples serve only to illustrate the preparation and use of the compounds according to the invention. The invention is, however, not limited thereto.

EXAMPLE I

Preparation of a mixture of 2-ethoxy-4-methyl- and 2-ethoxy-5-methylphenol 1.05 mole equivalents of diethylsulphate were slowly added dropwise to a solution of 1.0 mole of 4-methylcatechol in 420 g of 10% sodium hydroxide solution (1.05 mole equivalents of NaOH) at 50° C. The reaction mixture was then stirred for a further 2 hours at 50°-60° C. After cooling the reaction mixture was acidified and then extracted with ether.

The ether solution was concentrated by evaporation and the residüe distilled under reduced pressure, an approximately 1:1 mixture of 2-ethoxy-4-methyl and -5-methylphenol being obtained in a yield of 80%. Boiling point: 76°-77° C./40 Pa; $n_D^{20}=1.5237$.

The mixture had a pleasant and very natural odor of vanilla.

EXAMPLE II

Preparation of 2-ethoxy-4-ethylphenol

A suspension of methyltriphenylphosphonium bromide (1.15 mole) and potassium tert-butylate (1.33 moles) in 1 liter toluene was stirred for 1 hour at room temperature. 1.0 mole of ethylvanillin was added to the ylide thus formed. The reaction mixture was stirred for another hour and then washed with dilute hydrochloride acid. The solution was concentrated by evaporation and the residue distilled under reduced pressure. In this way 2-ethoxy-4-vinylphenol was obtained in a yield of 55%. Boiling point: 75° C./15 Pa.

This was dissolved in 400 ml of ethanol, 1 g of 5% Pd/C hydrogenating catalyst was added and the reaction mixture was hydrogenated at 400 kPa until the theoretical quantity of $H_2$ had been absorbed. After the catalyst had been filtered off, the reaction mixture was concentrated by evaporation. The residue was distilled under reduced pressure, 2-ethoxy-4-ethylphenol being obtained in a yield of 95%. Boiling point: 60° C./20 Pa.

The compound had a pleasant, somewhat sweet spicy odor of vanilla.

EXAMPLE III

A soap perfume for white soap was prepared according to the following recipe:

| | |
|---|---|
| jasmine absolute, synthetic | 110 parts by weight |
| α-hexylcinnamaldehyde | 90 parts by weight |
| 5-acetyl-3-isopropyl-1,1,2,6-tetramethylindan | 90 parts by weight |
| lily of the valley, absolute synthetic | 80 parts by weight |
| 4-tert-butylcyclohexyl acetate | 75 parts by weight |
| benzyl salicylate | 70 parts by weight |
| bergamot oil, synthetic | 65 parts by weight |
| rose oil, synthetic | 50 parts by weight |
| 3-(4-tert-butylphenyl)propanal | 50 parts by weight |
| linalool | 50 parts by weight |
| 4-(4-hydroxy-4-methylpentyl)cyclohexene-3-carbaldehyde | 45 parts by weight |
| phenylethyl amyl ether | 30 parts by weight |
| styrallyl propionate | 25 parts by weight |
| lavandin oil | 20 parts by weight |
| mousse d'abre absolute, colourless | 15 parts by weight |
| undecylenealdehyde | 10 parts by weight |
| amber oxide* | 10 parts by weight |
| galbanum oil, synthetic | 5 parts by weight |
| γ-undecalactone | 5 parts by weight |
| decanal | 5 parts by weight |
| 2-ethoxy-4-ethylphenol | 60 parts by weight |

-continued

| | |
|---|---|
| Total | 1000 parts by weight |

EXAMPLE IV

A cream perfume was prepared according to the following recipe:

| | |
|---|---|
| β-phenylethanol | 130 parts by weight |
| absolute of lily of the valley, synthetic | 125 parts by weight |
| acetylcedrene | 100 parts by weight |
| 5-acetyl-3-isopropyl-1,1,2,6-tetramethylindan | 100 parts by weight |
| benzyl salicylate | 80 parts by weight |
| citronellol | 70 parts by weight |
| 3-(4-tert-butylphenyl)propanal | 65 parts by weight |
| bergamot oil, synthetic | 50 parts by weight |
| linalool | 50 parts by weight |
| 3-isocamphylcyclohexanol | 50 parts by weight |
| jasmine absolute | 30 parts by weight |
| 2-heptylcyclopentanone | 30 parts by weight |
| α-terpineol | 25 parts by weight |
| mandarin oil, Italian | 20 parts by weight |
| mimosa absolute | 20 parts by weight |
| undecylene aldehyde* | 10 parts by weight |
| cis-3-hexenyl salicylate | 10 parts by weight |
| rose oxide* | 10 parts by weight* |
| decalactone | 5 parts by weight |
| mixture of phenols obtained according to Example I | 20 parts by weight |
| Total | 1000 parts by weight |

*10% solution in dipropyleneglycol

EXAMPE V

Two types of vanilla-perfumed toilet soap were prepared by mixing two times 1 kg of white soap grains in a soap mill with 10 g of 2-ethoxy-4-methylphenol and 10 g of vanillin respectively. The white soap flakes obtained this way were pressed into toilet soap bags in the conventional way.

The two types of fresh toilet soap had a pleasant odor of vanilla, but the soap perfumed with 2-ethoxy-4-methylphenol had a much stronger odor than the soap perfumed with vanillin.

Both types of soap were kept unpacked at room temperature and exposed to daylight.

After only a few days the soap perfumed with vanillin exhibited a marked brown discoloration and a deviation in odor was perceptible. After a few weeks this soap was discoloured dark brown not only on the surface, but right through. The odor of vanilla had completely disappeared and had been replaced by a faint, somewhat phenolic odor.

On the other hand, the soap perfumed with 2-ethoxy-4-methylphenol was still hardly discoloured even after half a year (somewhat cream-coloured on the surface and still white inside), while the odor strength had somewhat diminished but had not changed in character.

We claim:

1. A perfume composition comprising fragrance materials and an effective odorant amount of an ortho-alkoxyphenol having a structure according to the formula

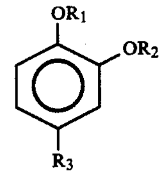

wherein one of the symbols $R_1$ or $R_2$ represents a hydrogen atom and the other an ethyl or propyl group and $R_3$ represents a methyl or ethyl group.

2. A perfume composition according to claim 1 wherein the ortho-alkoxyphenol is present at a level of at least 10 ppm by weight.

3. A perfume composition according to claim 2, wherein the ortho-alkoxyphenol is selected from the group consisting of 2-ethoxy-4-methyl-phenol, 2-ethoxy-5-methyl-phenol, and 2-ethoxy-4-ethyl-phenol.

4. A perfumed product comprising an effective odorant amount of an ortho-alkoxyphenol having the formula

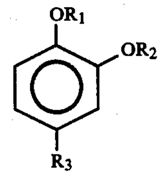

wherein one of the symbols $R_1$ or $R_2$ represents a hydrogen atom and the other an ethyl or propyl group and $R_3$ represents a methyl or ethyl group.

5. The perfumed product of claim 4, wherein the ortho-alkoxyphenol is selected from the group consisting of 2-ethoxy-4-methyl-phenol, 2-ethoxy-5-phenol, and 2-ethoxy-4-ethyl-phenol.

6. A vanilla-perfumed toilet soap comprising an effective odorant amount of an ortho-alkoxyphenol having a structure according to the formula

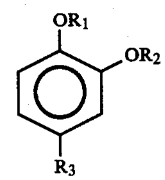

wherein one of the symbols $R_1$ and $R_2$ represents a hydrogen atom and the other an ethyl or propyl group and $R_3$ represents a methyl or ethyl group.

7. The toilet soap of claim 6, wherein the orthoalkoxyphenol is selected from the group consisting of 2-ethoxy-4-methyl-phenol, 2-ethoxy-5-methyl-phenol, and 2-ethyloxy-4-ethyl-phenol.

8. A toilet soap of claim 6, wherein the orthoalkoxyphenol is 2-ethoxy-4-methyl-phenol.

9. A toilet soap comprising fragrance materials and an effective odorant amount of an ortho-alkoxyphenyl having a structure according to the formula

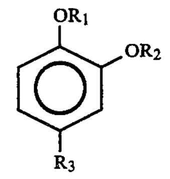

wherein one of the symbols $R_1$ or $R_3$ represents a hydrogen atom and the other an ethyl or porpyl group and $R_3$ represent a methyl or ethyl group.

10. The toilet soap of claim 9, wherein the ortho-alkoxyphenol is selected from the group consisting of 2-ethoxy-4-methylphenol, 2-ethoxy-5-methylphenol and 2-ethoxy-4-ethylphenol.

11. The toilet soap of claim 9, wherein the ortho-alkoxyphenol is 2-ethoxy-4-methylphenol.

12. The toilet soap of claim 9, wherein the ortho-alkoxyphenol is 2-ethoxy-4-ethylphenol.

* * * * *

UNITED STATES PATENT AND TRADEMARK OFFICE

CERTIFICATE OF CORRECTION

PATENT NO. : 4,650,604

Page 1 of 2

DATED : March 17, 1987

INVENTOR(S) : BROEKHOF, Nicolaas L.J.M.; VAN DER WEERDT, Antonius J.A.

It is certified that error appears in the above-identified patent and that said Letters Patent is hereby corrected as shown below:

First page, first line of Item 73, delete "501".

First page, 2nd column, 3rd-from-bottom line of ABSTRACT, "$R_1$ and $R_2$" should read -- $R_1$ or $R_2$ --.

Column 1, line 11, "solar" should read -- odor --.

Column 1, line 13, "order" should read -- odor --.

Column 1, line 14 "use" should read -- vanillin, --.

Column 1, line 52, "additionally" should read -- additional --.

Column 2, line 42, "material with the characteristic ordor" should read -- materials with the characteristic odor --.

Column 2, line 48, "$R_1$ and" should read -- $R_1$ or --.

Column 2, line 52, "odor" should read -- odors --.

Column 3, line 26, "3-cyclohexancarbaldehyde" should read -- cyclohexene-3-carbaldehyde --.

Column 3, line 27, "3-cyclohexenecarbaldehyde" should read -- cyclohexene-3-carbaldehyde --.

Column 3, line 28, delete "3-acetoxy-".

Column 3, line 39, after "indan musks" insert -- , --.

Column 3, line 49 "perfume" should read -- perfumed --.

Column 3, line 63, "porportionally" should read -- proportionally --.

Column 4, line 65 "amber oxide" has an asterisk after it, with no footnote to Example III indicating what it means.

Column 4, line 67 "γ-undecalactone" should read -- α-undecalactone --.

Column 5, line 36 "EXAMPE" should read -- EXAMPLE --.

Column 5, line 42, "bags" should read -- bars --.

Column 6, line 40, "2-ethyoxy-5-phenol" should read -- 2-ethoxy-5-methyl-phenol --.

Column 8, lin 1, "$R_3$" should read -- $R_2$ --.

UNITED STATES PATENT AND TRADEMARK OFFICE

CERTIFICATE OF CORRECTION

PATENT NO. : 4,650,604

DATED : March 17, 1987

INVENTOR(S) : BROEKHOF, Nicolaas L.J.M.; VAN DER WEERDT, Antonius J.A.

It is certified that error appears in the above-identified patent and that said Letters Patent is hereby corrected as shown below:

Column 8, line 2 "porpyl" should read -- propyl --.
Column 8, line 3, "represent" should read -- represents --.

Signed and Sealed this

Twenty-second Day of September, 1987

*Attest:*

DONALD J. QUIGG

*Attesting Officer* *Commissioner of Patents and Trademarks*